US00PP12434P2

(12) United States Plant Patent
Noodelijk

(10) Patent No.: US PP12,434 P2
(45) Date of Patent: Mar. 5, 2002

(54) CHRYSANTHEMUM PLANT NAMED 'SIRENA'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/563,253

(22) Filed: May 1, 2000

(51) Int. Cl.[7] ..... A01H 5/00
(52) U.S. Cl. ..... Plt./292
(58) Field of Search ..... Plt./292, 291, 286

*Primary Examiner*—Bruce R. Campell
*Assistant Examiner*—June Hwu
(74) *Attorney, Agent, or Firm*—Parkhurst & Wendel, L.L.P.

(57) ABSTRACT

A chrysanthemum plant named SIRENA characterized by its medium sized blooms with pink ray florets and prolific branching; natural season flower date Aug. 28–31; blooming for a period of 7 weeks.

2 Drawing Sheets

BACKGROUND OF THE INVENTION

The new plant of the present invention comprises a new and distinct cultivar of Chrysanthemum plant that is a cross of unknown *Dendranthema Grandiflora* parents. The new and distinct cultivar was a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in August 1996. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
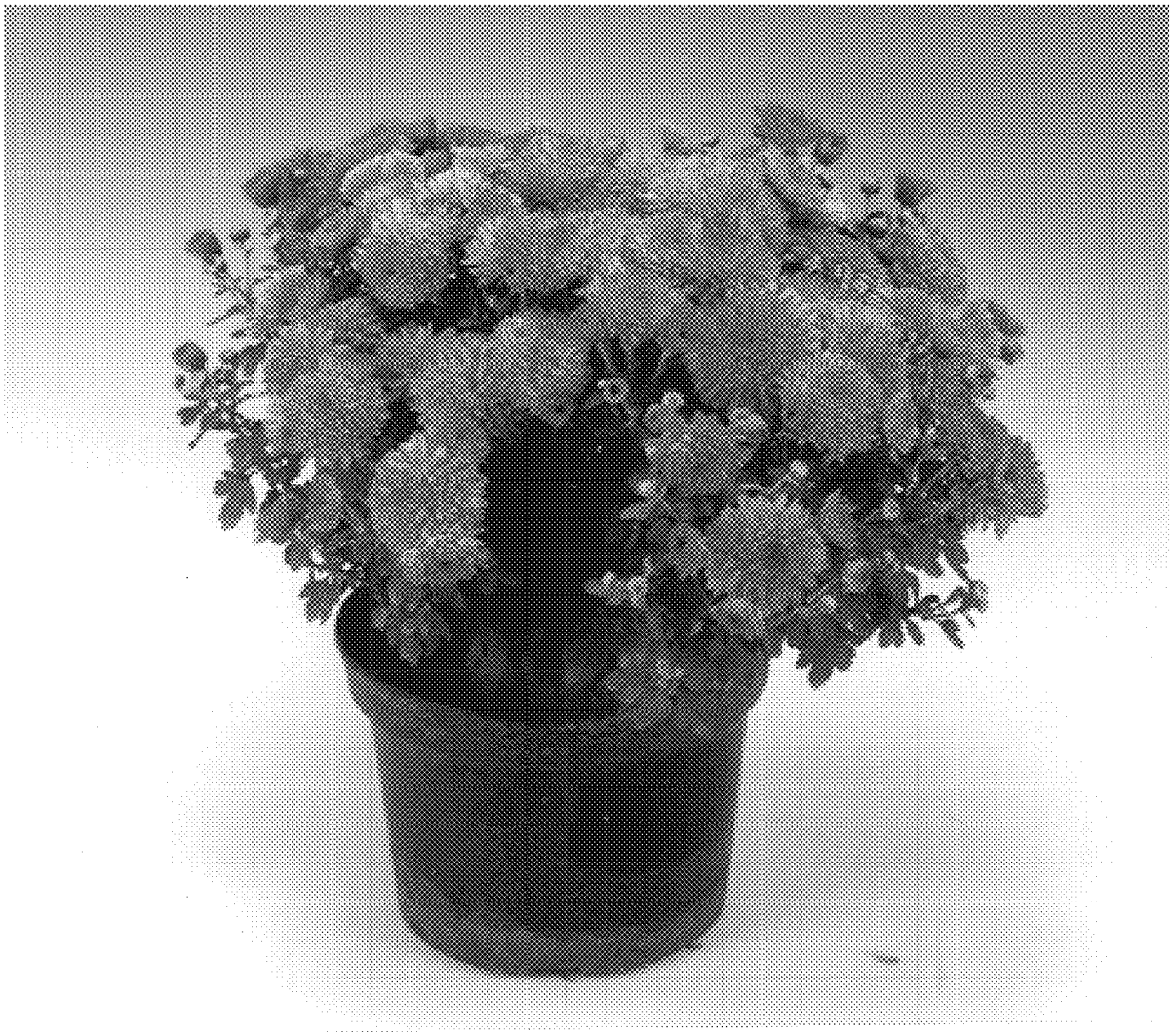
FIG. 1 shows a plant of the cultivar in full bloom.
Figure 2:
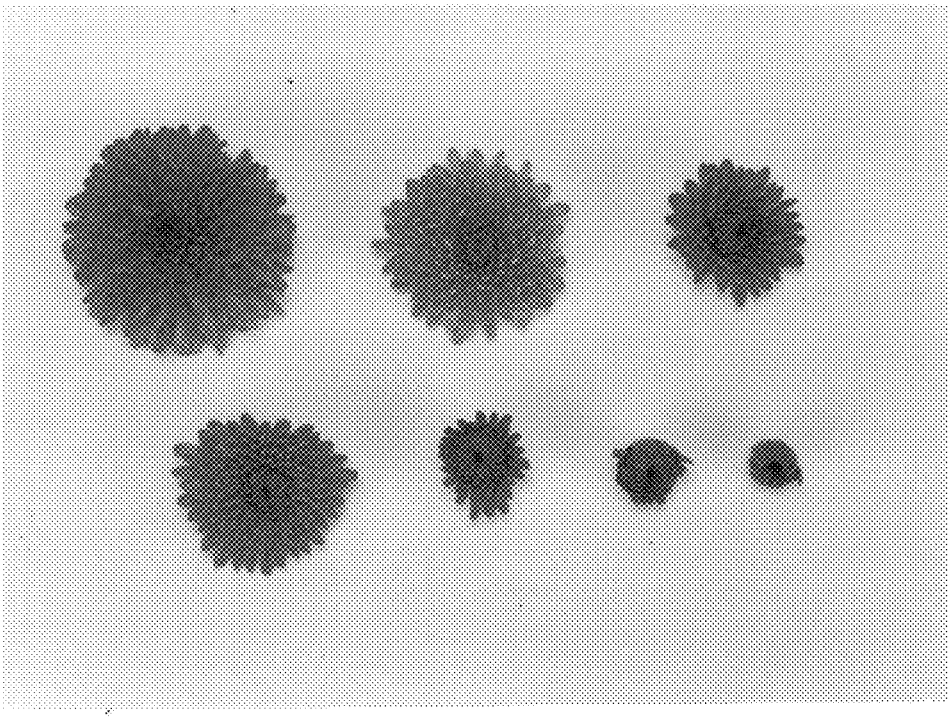
FIG. 2 shows the various stages of bloom of the new cultivar.
Figure 3:
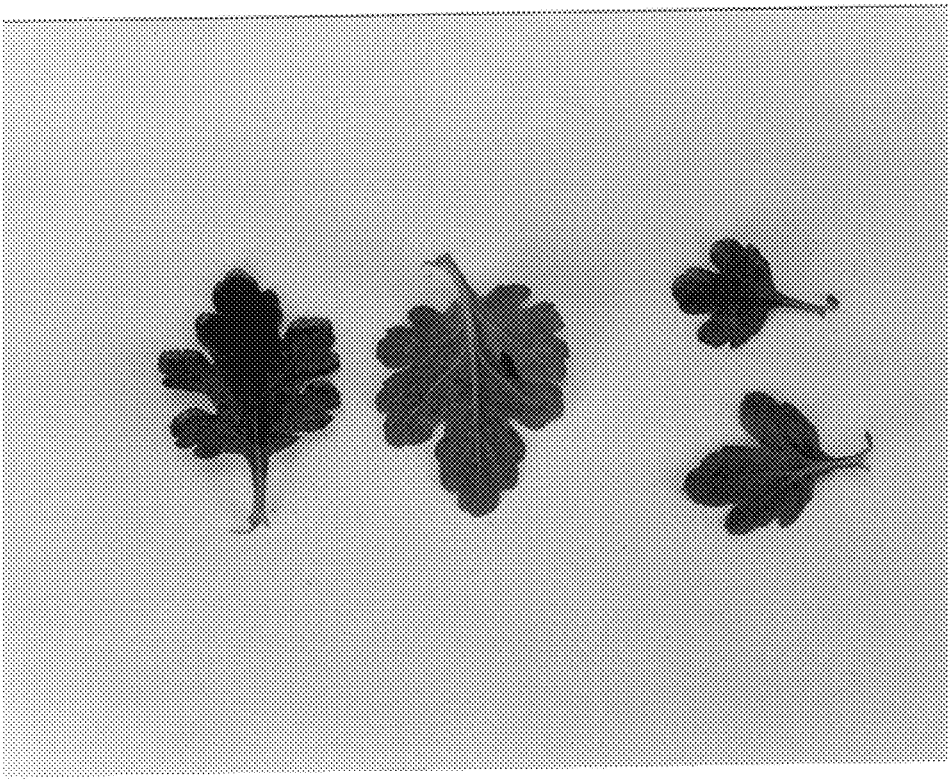
FIG. 3 shows the various stages of foliage and petiole of the new cultivar.

This new variety of chrysanthemum is of the botanical classification *Dendranthema Grandiflora*. The observations and measurements were gathered from plants grown out door in Rijsenhout, Holland under natural day length and temperature and planted week 22 in 1997 and 1998. The natural blooming date of this crop was Aug. 28–31 (week 35). The average height of the plants was 28–31 cms. This new variety produces medium sized decorative blooms with pink ray florets.

The following is a description of the plant and characteristics that distinguish SIRENA as a new and distinct variety.

The color designations are taken from the plant itself. Accordingly, any discrepancies between the color designations and the colors depicted in the photographs are due to photographic tolerances. The actual color on the plant is more blue and less red.

Botanical Classification CULTIVAR SIRENA

Bud:
- *Size.*—Medium, cross-section +/−1.5 cm height +/−1.5 cm.
- *Outside color.*—Red-purple 74 D.

Bloom:
- *Size.*—Medium.
- *Fully expanded.*—5.5–6.0 cm.
- *Borne*(*number of blooms per branch*).—Upper and lower portion plural blooms per branch (approx. 6 blooms per branch).
- *Length of lateral branch.*—From top till bottom 12 cm.
- *Lateral branch, attachment branching.*—Prolific with 6–8 breaks after pinching.
- *Form.*—Decorative.
- *Performance* (*on the plant*).—7 weeks.

Color:
- *Center of flower.*—Immature Red-purple 72 C. Mature Red-purple 72 C.
- *Color of the upper surface of the majority of the ray-florets.*—Red-purple 72 C.
- *Color of the lower surface of the majority of the ray-florets.*—Red-purple 74 D.
- *Tonality from distance.*—A decorative garden mum with pink blooms.
- *Discoloration.*—To Red-purple 73 A.

Ray florets:
- *Texture.*—Upper side and under side smooth.
- *Number.*—+/−200–230.
- *Cross-section.*—Concave.
- *Longitudinal axis of the majority.*—Incurved.
- *Shape of tip.*—Pointed.

Cultivar sirena:
- *Fragrance.*—Typical chrysanthemum.
- *Disc diameter* (*natural season crop when visible*).—Not present.

Reproductive organs:
- *Stamen.*—None.
- *Pollen.*—None.
- *Styles* (*present in both ray and disc florets*).—Green, thin.
- *Style length.*—+/−4 mm.
- *Stigmas.*—Yellow-green.
- *Stigma width.*—+/−1 mm.
- *Ovaries.*—Enclosed in calyx.

Plant:

*Form.*—A garden mum (pot mum) meant for outdoor use.

*Growth.*—Compact.

*Height* (*from soil level*).—28–31 cm.

*Stem color.*—Green 138 B.

*Stem strength.*—Medium.

*Stem brittleness.*—Present.

*Stem anthocyanin coloration.*—Absent.

*Natural blooming date.*—August 28–31.

Foliage:

*Color.*—Upper side green 137 A. Under side green 137 C.

*Size.*—Small, length +/−6.0 cm width +/−5.0 cm.

*Quantity* (*number per lateral branch*).—10–12.

*Shape.*—Egg-shaped.

*Texture.*—Fleshy.

*Ribs and veins.*—Ribs and veins well developed.

*Edge.*—Round (lobed).

*Shape of base of sinus between lateral lobes.*—Round.

*Margin of sinus between lateral lobes.*—Diverging.

*Shape of base.*—Cordate.

Cultivar sirena:

*Apex.*—Cuspidate.

I claim:

1. A new and distinc variety of chrysanthemum plant as described and illustrated.

* * * * *